United States Patent [19]

Kraus et al.

[11] 4,338,190
[45] Jul. 6, 1982

[54] PERITONEAL ARTIFICIAL KIDNEY

[75] Inventors: Menahem A. Kraus; Moshe A. Frommer, both of Rehovot, Israel

[73] Assignee: A. T. Ramot Plastics Ltd., Tel Aviv, Israel

[21] Appl. No.: 766,581

[22] Filed: Feb. 8, 1977

[30] Foreign Application Priority Data

Feb. 13, 1976 [IL] Israel .......................................... 49031

[51] Int. Cl.³ .............................................. B01D 31/00
[52] U.S. Cl. .............................. 210/195.2; 128/213 A; 210/259; 210/321.3
[58] Field of Search ............... 210/259, 321 R, 321 B, 210/195.2; 128/214 R, 213 A

[56] References Cited

U.S. PATENT DOCUMENTS

| | | | |
|---|---|---|---|
| 3,506,126 | 4/1970 | Serfass et al. | 210/259 X |
| 3,579,441 | 5/1971 | Brown | 210/259 X |
| 3,774,763 | 11/1973 | Yall et al. | 210/259 X |
| 3,799,873 | 3/1974 | Brown | 210/321 B X |
| 3,825,493 | 7/1974 | Brown et al. | 210/321 R X |
| 3,839,200 | 10/1974 | Gigou et al. | 210/259 X |
| 3,946,731 | 3/1976 | Lichtenstein | 210/90 |
| 4,081,372 | 3/1978 | Atkin | 128/214 R X |

FOREIGN PATENT DOCUMENTS 1198032  7/1970  United Kingdom ............ 210/321 B

Primary Examiner—Frank A. Spear, Jr.
Attorney, Agent, or Firm—Benjamin J. Barish

[57] ABSTRACT

An artificial kidney comprises means for introducing a prepared solution into the peritoneal cavity to draw toxic metabolites therefrom into the fluid, the fluid exiting from the cavity as peritoneal fluid; and a dialysis or ultrafilter separator containing a selective membrane having a high permeability to low molecular weight toxic metabolites but a low permeability to high molecular weight protein. The peritoneal fluid is circulated through the separator on one side of the selective membrane in the above-described closed-loop peritoneal circuit, the fluid exiting from that side of the membrane being returned to the peritoneal cavity. The artificial kidney further includes a single-pass reconstitution circuit wherein tap water is introduced into the inlet of a hyperfilter impermeable to ions and to organic matter; and a concentrate including sugar and salts is introduced into the water exiting from the permeate outlet of the hyperfilter to form a water concentrate solution. The resulting water-concentrate solution is utilized for maintaining substantially constant the original concentration of sugar and salt in the peritoneal fluid as the waste metabolites, passing through the separator, are removed from the peritoneal fluid.

2 Claims, 7 Drawing Figures

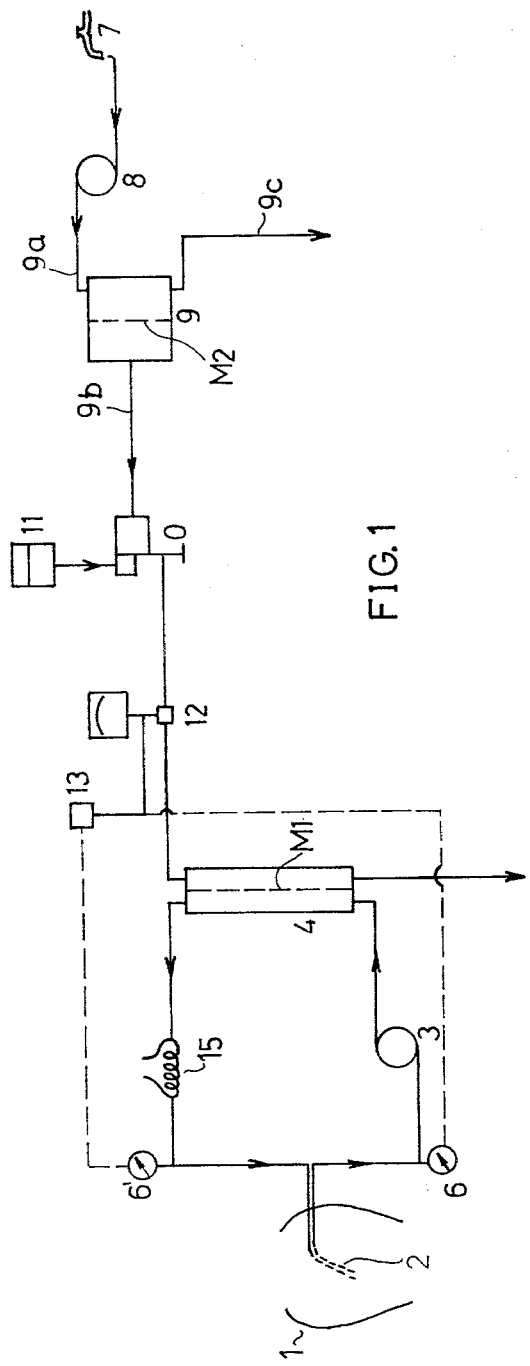
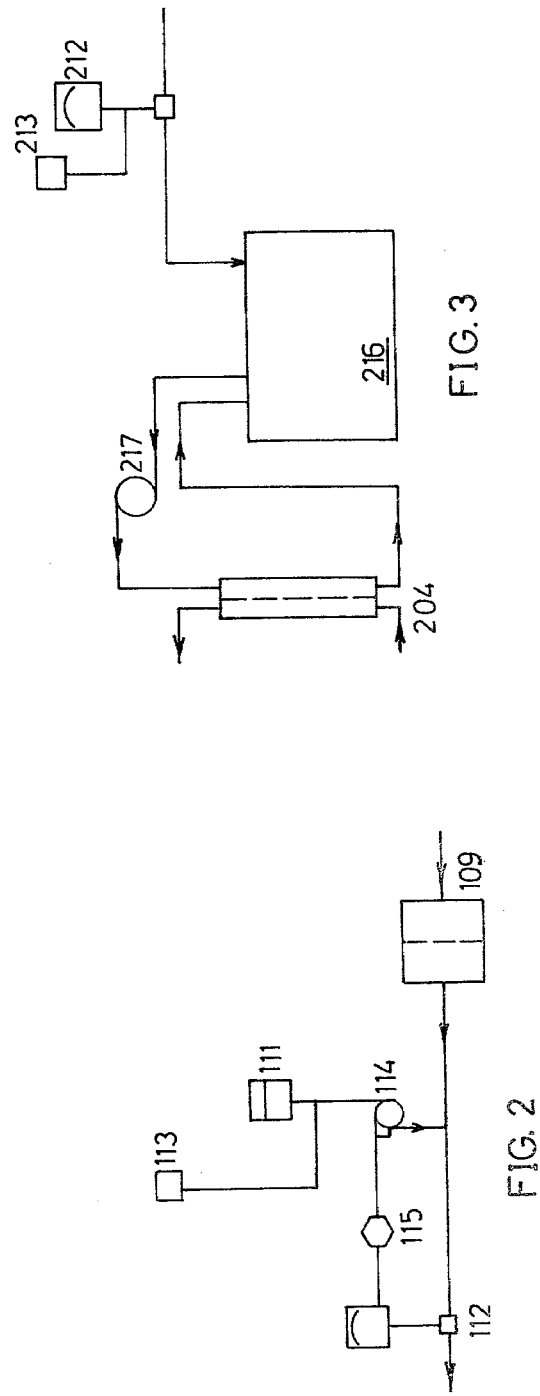

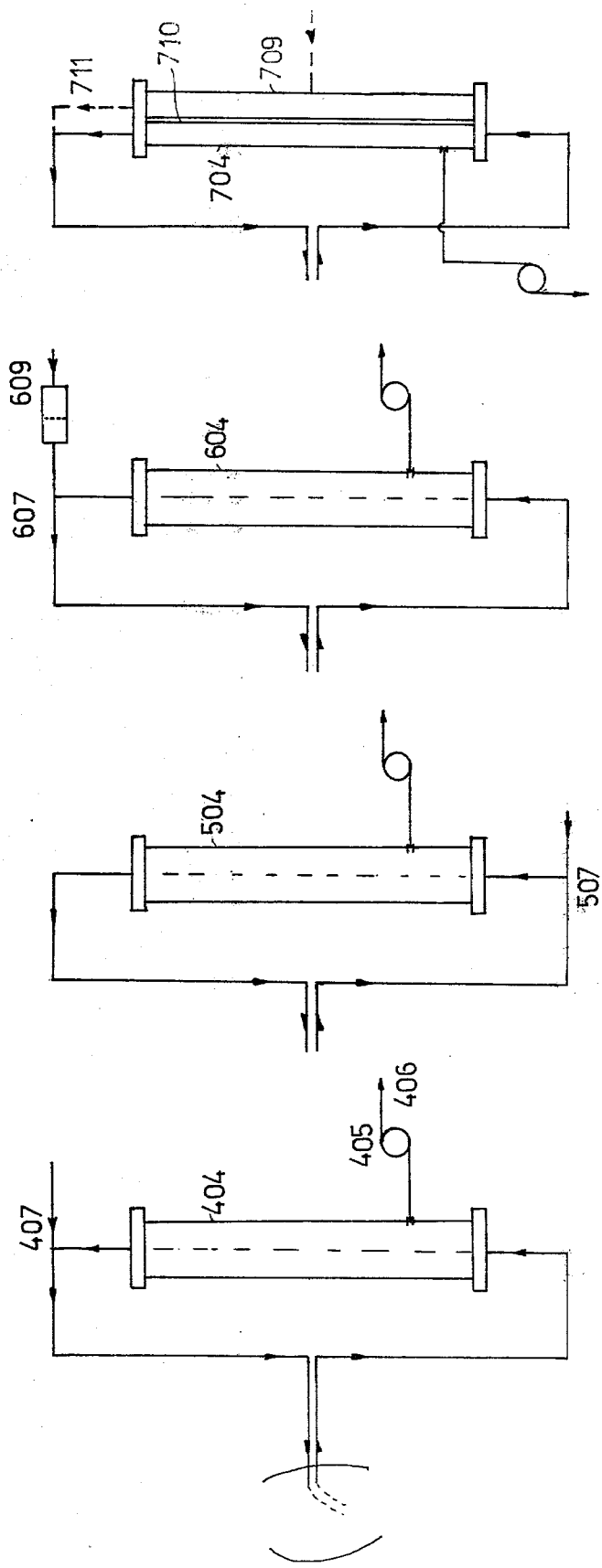

PERITONEAL ARTIFICIAL KIDNEY

BACKGROUND OF THE INVENTION

The present invention relates to artificial kidneys and particularly to a peritoneal artificial kidney for removing toxic substances from the peritoneal cavity.

Artificial kidneys based on peritoneal dialysis are increasingly being used as a treatment for patients suffering from renal insufficiency. In peritoneal dialysis, a sterile dialysis solution is infused into the peritoneal cavity, and after absorbing waste metabolites, it is discarded, the process being repeated. This dialysis method has been used mainly with patients where hemodialysis is not feasible for various physiological reasons. However, this technique is increasingly becoming more attractive for general application for a number of reasons, including its great simplicity, its avoidance of involving blood directly, and its probably better removal of toxic metabolites of molecular weight of 300–1500 ("middle molecules"). These advantages, particularly the fact that blood vessels are not involved, make this method highly attractive for home dialysis since, as distinguished from hemodialysis, there is no life danger in case of a mechanical malfunction such as a leaking tube or air bubbles.

Machines for peritoneal dialysis commercially available today are basically of two types. One is simply a timer operating in conjunction with a large reservoir of sterile dialysing solution. The time for inflow, dwell and outflow can be predetermined as desired. A more sophisticated machine serves both as a timer and as an automatic mixing machine. The dialysing solution is prepared by the machine using tap water purified by reverse osmosis and a concentrate of salts and sugar. In the latter machine, a heat sterilisation step is required by health authorities. This makes it more complicated and expensive. Also, the dialysis using such a machine (as all conventional peritoneal dialysis) is relatively inefficient, giving urea clearances of 20–25 ml/min.

BRIEF SUMMARY OF THE INVENTION

An object of the present invention is to provide a peritoneal artificial kidney having advantages in the above respects.

According to the present invention, there is provided a peritoneal artificial kidney comprising a closed-loop peritoneal circuit including means for introducing a prepared solution into the peritoneal cavity to draw toxic metabolites therefrom into the fluid, the fluid exiting from the cavity as peritoneal fluid; a separator containing a selective membrane having a high permeability to low molecular weight toxic metabolites but a low permeability to high molecular weight protein; and means for circulating the peritoneal fluid through the separator on one side of the selective membrane, the fluid exiting from that side of the membrane being returned to the peritoneal cavity. The artificial kidney further includes a single-pass reconstitution circuit including: a hyperfilter impermeable to ions and to organic matter, and having an inlet, a permeate outlet, and a residue outlet; means for introducing tap water into the inlet of the hyperfilter; means for introducing a concentrate including sugar and salts into the water exiting from the permeate outlet of the hyperfilter to form a concentrate solution; and means for utilizing the resulting concentrate solution for maintaining substantially constant the original concentration of sugar and salt in the peritoneal fluid as the waste metabolites, passing through the separator, are removed from the peritoneal fluid.

In the preferred embodiments of the invention described below, the hyperfilter is a reverse osmosis unit.

Preferably the separator is a dialyser, and the last-named means introduces the water-concentrate solution into the dialyser on the other, non-body loop, side of the selective membrane. However, it is contemplated that the separator could also be an ultra-filter, in which case the last-named means introduces the water-concentrate solution into the fluid being returned to the peritoneal cavity.

It is thus seen that in the artificial kidney constructed in accordance with the invention, there is no need for heat sterilisation, as two different membranes (the hyperfilter and the separator membranes), being impermeable to bacteria, protect the body from any contamination contained in the tap water. Also, protein loss, which usually accompanies peritoneal dialysis, is prevented. Further, the peritoneal fluid may be circulated through the peritoneal cavity at a high circulation rate which has been found to increase dialysis efficiency.

According to further features present in the preferred embodiments of the invention described below, the means for introducing the concentrate into the water exiting from the hyperfilter includes a mixing pump. This pump may be manually set to the desired ratio. On the other hand, and in accordance with a feature present in one of the described embodiments, the mixing pump may be controlled automatically to mix the desired ratio of concentrate and water by means of a conductivity meter which measures the conductivity of the concentrate solution exiting from the pump and controls the pump in response thereto.

According to another feature present in another described embodiment, the machine further includes a storage vessel for receiving concentrate solution leaving the dialyser on the other side of the selective membrane, and a recirculating pump for recirculating same from the reservoir back to the inlet of the dialyser on the other side of the selective membrane.

Further features and advantages of the invention will be apparent from the description below.

BRIEF DESCRIPTION OF THE DRAWINGS

The invention is herein described, somewhat diagrammatically and by way of example only, with reference to the accompanying drawings, wherein:

FIG. 1 diagrammatically illustrates one form of peritoneal artificial kidney constructed in accordance with the invention;

FIG. 2 illustrates a variation in the system of FIG. 1;

FIG. 3 illustrates a further variation in the system of FIG. 1; and

FIGS. 4–7 illustrate variations of the invention wherein the separator is an ultrafilter.

DESCRIPTION OF THE PREFERRED EMBODIMENTS

In FIG. 1, the patient receiving the peritoneal dialysis treatment is generally designated 1. The machine is connected to him by means of a double indwelling peritoneal catheter 2 inserted into the patient's peritoneal cavity, this form of catheter providing for simultaneous inflow and outflow. A prepared solution is introduced into the peritoneal cavity to draw toxic substances therefrom into the fluid, and the fluid exits from the cavity as peritoneal fluid.

The machine includes a pump 3 and a dialyser 4 containing a selective membrane M1 having a high permeability to low molecular weight toxic metabolites, but a low permeability to high molecular weight protein. Pump 3 introduces a pressure gradient which forces the peritoneal fluid drawn from the peritoneal cavity by catheter 2 through the dialyser 4 on one side of the selective membrane M1, the fluid exiting from the dialyser and being returned on catheter 2 for reintroduction into the peritoneal cavity. A heating element 15 is provided, for example in this return path of the peritoneal fluid, to heat it before its introduction into the peritoneal cavity. In addition, a pressure gauge 6 is provided in the dialyser feed line between catheter 2 and pump 3, and another pressure gauge 6' is provided in the return line between heater 15 and catheter 2. These gauges produce indications of extreme inflow (positive) or outflow (negative) pressure build-ups, for example because of clogging in the circuit.

Water supplied from a water tap 7 is pumped by a high pressure pump 8 through a hyperfilter in the form of a reverse osmosis unit 9. The latter unit includes a reverse osmosis membrane M2, the tap water being introduced by pump 8 into the inlet 9a to contact one side of the membrane. Membrane M2 is of a type which is impermeable to ions and to organic matter, and therefore it purifies and sterilizes the water from tap 7. The so-purified and sterilized water exiting from the reverse osmosis unit 9 through the permeate outlet 9b is then mixed in mixer 10 with a concentrate of sugar and salts supplied by a reservoir 11. This concentrate is mixed at the desired ratio with the water. The mixing may be done, for example, by using a duplex pump for mixer 10, such as a double diaphragm, piston or peristaltic pump, which may be set manually to the desired ratio. The residue exits through the residue outlet 9c.

The concentrate solution exiting from mixer 10 is then pumped through a conductivity meter 12 provided with a meter indicating the concentration of this fluid. Conductivity meter 12 may be connected to an alarm 13, as shown by the broken lines, to actuate same in case of extremely high or low conductivity of the dialysing solution. Alarm 13 may also be connected to pressure gauges, 6, 6', so as also to be actuated in case of extreme inflow or outflow of pressure build-ups that may be caused by clogging, as mentioned above.

As also indicated above, the peritoneal fluid introduced into the peritoneal cavity, is protected from any contamination or bacteria originally present in the tap water since it passes through two different membranes, namely membrane M2 of the reverse osmosis unit 9, and membrane M1 of the dialyser 4. Accordingly, there is no need for any heat sterilization or additional purification of the peritoneal fluids before being reintroduced into the peritoneal cavity. Also, because the selective membrane M1 in the dialyser 4 has a low permeability to high molecular weight molecules, protein loss, which usually accompanies peritoneal dialysis, is minimized.

It will thus be seen that the machine operates by circulating the peritoneal solution through a closed loop peritoneal circuit including dialyser 4, which solution is continuously dialysed and reconstituted, via a single-pass reconstitution circuit, by a solution automatically prepared from tap water and concentrate. Thus, unlike conventional peritoneal dialysis, the dialysis with the novel machine is continuous and is not a batch process.

Removal of water from the peritoneum may be achieved by providing a pressure gradient across the dialyser membrane dialyser 4, this being effected by controlling pump 3. When water removal is not desired pressure across these membranes should be zero. This may be achieved, for example, by having a sterile opening to the atmosphere, at both the "peritoneal" and "tap" sides of dialyser 4.

FIG. 2 illustrates a variation wherein fixing the ratio of pure water to the concentrate of sugar and salts is effected, not manually, by presetting the mixer (10), but rather automatically, under the control of the conductivity meter. Thus, as shown in FIG. 2, the pure and sterilized water leaving the reverse osmosis unit 109 receives concentrate from reservoir 111 via pump 114, and the concentrate solution is passed through conductivity meter 112, the latter not only indicating the actual proportions, but also providing an electrical signal via an electronic steering device 115 to control pump 114 to cause it to meter the concentrate to the water at the desired rate.

In FIG. 1, the dialysing solution is prepared continuously and is discarded continuously. FIG. 3 illustrates a variation wherein it may be prepared in batches, stored in a storage vessel from which it is recirculated during dialysis, and periodically renewed. Thus, as shown in FIG. 3, the machine includes a storage vessel 216 interposed between the conductivity meter 212 having an indicator or alarm 213, and the input to the dialyser 204. The prepared concentrate solution is introduced into the storage vessel and is recirculated from the vessel to the dialyser by means of another pump 217. After leaving the dialyser, it is returned back to storage vessel 216. Thus, the latter vessel need only be periodically renewed as and when fresh concentrate solution is required.

To avoid diminishing the natural good clearance of middle molecules by the addition of the artificial membrane, the latter membrane could be an ultrafilter instead of a dialysis membrane. This is schematically illustrated in FIGS. 4–7.

Thus, as shown in FIG. 4, the separator unit 404, instead of being a dialyser as described in FIGS. 1–3, is an ultrafilter containing a selective membrane having a high permeability to low molecular weight toxic metabolites, but a low permeability to high molecular weight protein. Such ultrafilter membranes may be in the form of flat sheets or hollow fibres. The peritoneal solution is circulated in the body loop (i.e., the closed-loop peritoneal circuit) past one side of the ultrafiltration membrane in unit 404, while ultrafiltration is obtained by means of a pump 405 on the other side of the membrane. The ultrafiltrate, which contains low and middle molecular weight waste metabolites, but not proteins, is discarded at 406. An equal volume of sterile water-concentrate solution is added, via the single-pass reconstitution circuit, to the peritoneal loop at point 407 for return to the peritoneal cavity in order to maintain substantially constant the original concentration of sugar and salt in the peritoneal fluid.

FIG. 5 illustrates a variation wherein this water-concentrate solution is added to the body loop at point 507 before the fluid in that loop is passed through the ultrafilter 504.

Such an artificial kidney has the following advantages:

(1) High clearance due to high circulation rate.

(2) Minimal protein loss because of the impermeability of the UF membrane to proteins.

(3) No sterility problems as the UF membrane is an excellent bacterial filter.

(4) Good removal of both small and middle molecular weight waste metabolites.

(5) Because of the good clearance attainable by ultrafiltration, relatively low ultrafiltration rates suffice and thus no large amounts of sterile reconstitution solution are needed. Thus at an ultrafiltration rate of 40 ml/min about the same amount of sterile solution is used as in conventional peritoneal dialysis.

By designing the ultrafilter in the appropriate form and size it may be worn by the patient constantly (also when not connected to the dialysis machine), and thus no direct access to the peritoneal loop is necessary for starting the treatment.

FIG. 6 illustrates an arrangement wherein the sterile reconstitution solution is prepared in situ by using tap water to which a salt and sugar concentrate is added and hyperfiltered by a reverse osmosis unit (not shown, but as in FIG. 1), and then ultrafiltered at 609. This reconstituted solution is added to the body loop at point 607 on the output side of the main ultrafilter 604.

FIG. 7 illustrates the variation wherein the additional ultrafilter, instead of being a separate unit 609 as in FIG. 6, is a compartment 709 in the main ultrafilter 704, separated from the rest of the membranes by a water impermeable wall 710. The main compartment 704 serves for ultrafiltration out of the peritoneum, and the additional compartment 709 at the other side of membrane 710 serves for ultrafiltration into the peritoneum. In case of a hollow fire ultrafilter, the fibres in the compartment of unit 709 may be potted at their lower ends, and thus reconstitution solution flows in only at the upper openings at point 711.

Many other variations, modifications and applications of the illustrated embodiments will be apparent.

What is claimed is:

1. An artificial kidney including a peritoneal dialysis system which prevents protein loss, permits the peritoneal fluid to be circulated through the peritoneal cavity at a high circulation rate, and obviates the need for heat sterilization, comprising: a closed-loop peritoneal circuit including means for introducing a prepared solution into the peritoneal cavity to draw toxic metabolites therefrom into the fluid, the fluid exiting from the cavity as peritoneal fluid, a separator containing a selective membrane having a high permeability to low molecular weight toxic metabolites but a low permeability to high molecular weight protein, and means for circulating the peritoneal fluid through the separator on one side of the selective membrane, the fluid exiting from that side of the membrane being returned to the peritoneal cavity; and a single-pass reconstitution circuit including a hyperfilter impermeable to ions and to organic matter, and having an inlet, a permeate outlet, and a residue outlet, means for introducing tap water into the inlet of the hyperfilter, means for introducing a concentrate including sugar and salts into the water exiting from the permeate outlet of the hyperfilter to form a water concentrate solution, and means for utilizing the resulting water-concentrate solution for maintaining substantially constant the original concentration of sugar and salt in the peritoneal fluid as the waste metabolites, passing through said separator, are moved from the peritoneal fluid, said separator being a dialyser, and said last-named means introducing said water-concentrate solution into the dialyser on the other side of the selective membrane.

2. An artificial kidney according to claim 1, wherein said separator is an ultrafilter, and wherein the last-named means introduces said water-concentrate solution into the fluid being returned to the peritoneal cavity.

* * * * *